United States Patent [19]

Castrogiovanni et al.

[11] Patent Number: 5,139,570
[45] Date of Patent: Aug. 18, 1992

[54] NAIL STAIN REMOVER

[75] Inventors: Anthony Castrogiovanni, Belford; Robert W. Sandewicz, Spotswood, both of N.J.; Cecilia Benedicto, Plainview, N.Y.

[73] Assignee: Revlon, Inc., New York, N.Y.

[21] Appl. No.: 690,460

[22] Filed: Apr. 24, 1991

[51] Int. Cl.⁵ .................. C09G 1/02; B08B 1/00; H45D 29/17; H61K 7/04
[52] U.S. Cl. ........................... 106/3; 252/163; 15/104.93; 15/104.94; 132/76.4; 424/61
[58] Field of Search .................. 106/3; 252/163; 15/104.93, 104.94; 51/307, 308; 132/76.4; 134/38; 424/61

[56] References Cited

U.S. PATENT DOCUMENTS

| | | | |
|---|---|---|---|
| 1,878,102 | 9/1932 | Bradley | 252/170 |
| 2,393,864 | 1/1946 | Fransisco | 252/170 |
| 2,971,920 | 2/1961 | Wurmbock | 252/170 |
| 3,150,048 | 9/1964 | Hollub | 424/61 |
| 3,441,645 | 4/1969 | McKissick | 424/61 |
| 3,729,569 | 4/1973 | Charle | 424/61 |
| 4,009,114 | 2/1977 | Yurko | 252/109 |
| 4,032,464 | 6/1977 | Mausner | 424/61 |
| 4,034,769 | 7/1977 | Nishimura | 132/76.4 |
| 4,071,333 | 1/1978 | Like | 106/3 |
| 4,129,527 | 12/1978 | Clark et al. | 252/528 |
| 4,137,302 | 1/1979 | Humbert | 424/61 |
| 4,181,633 | 1/1980 | Colodney et al. | 106/3 |
| 4,344,932 | 8/1982 | Gordon | 424/61 |
| 4,381,792 | 5/1983 | Busch, Jr. et al. | 132/76.4 |
| 4,407,722 | 10/1983 | Davies | 252/174 |
| 4,482,538 | 11/1984 | Davies | 424/61 |
| 4,485,037 | 11/1984 | Curtis | 134/38 |
| 4,530,726 | 7/1985 | Monteil | 134/38 |
| 4,572,222 | 2/1986 | Pangburn | 132/76.4 |
| 4,741,862 | 5/1988 | Kosal | 252/527 |
| 4,804,486 | 2/1989 | Day | 134/38 |
| 4,824,662 | 4/1989 | Hofman | 424/61 |
| 4,885,109 | 12/1989 | Umemoto | 252/174.21 |
| 4,966,609 | 10/1990 | Callinan et al. | 51/295 |
| 5,000,761 | 3/1991 | Mayton et al. | 106/3 |

Primary Examiner—Mark L. Bell
Assistant Examiner—Helene Klemanski
Attorney, Agent, or Firm—Julie Blackburn

[57] ABSTRACT

A nail cleansing composition useful for removing stains from human nails, nail stain removing kits, and a method for removing stains from nails using the composition of the invention.

13 Claims, No Drawings

NAIL STAIN REMOVER

TECHNICAL FIELD

A nail cleanser for human nails which removes various types of stains.

BACKGROUND OF THE INVENTION

The human nail is very porous and becomes more so with age. This porosity increases the tendency of nails to stain. Staining may be caused by the repeated use of nail lacquer over a prolonged period of time, nicotine from handling lighted cigarettes, or from various chemicals to which people may be exposed in their homes or occupations. Nails also yellow with age due to melamine, a brown pigment synthesized in the body by normal biological processes and carried up into the nails from the nail beds. The stains due to nail lacquers are believed to be caused by bleeding of pigmentary materials such as partially solubilized dyes into the nail. In addition, the nitrocellulose found in the nail lacquers is known to heavily contribute to nail staining. The esthetically displeasing result of stained nails has lead to different nail stain removers.

Many of the standard preparations use bleaches which are extremely drying and irritating to nails. Preparations containing strong alkali such as sodium hydroxide or alkali metal hydroxides are also known. For obvious reasons these preparations are not desirable.

In U.S. Pat. No. 4,344,932 a nail cleanser comprised of chelating agents such as EDTA and urea in a liquid carrier is disclosed. The chelating agents remove stains by complexing with the metal ions which are present in many nail stains. However some stains, such as residual dyestuffs left on nails due to lacquers, do not respond as effectively to chelating agents alone, thus resulting in a less effective cleanser. Further, urea is often irritating to tissues surrounding the nail so it is desirable to find nail cleansing preparations which avoid these drawbacks.

SUMMARY OF THE INVENTION

The invention is directed to a composition useful for removing stains from human nails comprising the following essential constituents in a cosmetically suitable vehicle:
a) an abrasive agent, and
b) one or more white pigments.

The invention is also directed to a nail stain removing kit comprised of single units of porous material containing the dehydrated composition set forth above, which unit is moistened with water immediately prior to use to yield a nail cleansing pad which is used to scrub the nails.

The invention is also directed to a nail stain removing kit comprised of a container filled with the composition of the invention.

The invention is also directed to a method for removing stains from human nails comprising cleansing nails with the composition set forth above.

DETAILED DESCRIPTION

The composition essentially contains an abrasive agent. Suitable abrasive agents include pumice, polyethylene granules, aluminum oxide, silica, magnesium aluminum silicate, kaolin, finely ground nut shells or diatomaceous earth. About 1-25% of abrasive agent is a suitable range. The preferred abrasive agent is pumice or magnesium aluminum silicate.

The composition also essentially contains one or more white pigments. The pigment functions by cosmetically obliterating surface nail stains. Pigments such as zinc oxide, titanium dioxide, barium sulfate, zinc sulfide are suitable, although titanium dioxide is preferred. A suitable range of white pigment is about 1-20%. The abrasive agent will polish nails by mechanical abrasion, while the stain residues are visually mitigated by the white residue left by the white pigment. The composition may additionally contain a variety of metallic salts such as aluminum chloride or aluminum chlorohydrate which react with residual dyestuffs on nails, as well as absorbents (e.g. talc, blanc fixe) and/or chelating agents (e.g. EDTA).

The essential constituents of the invention are contained in a cosmetically suitable vehicle such as an oil in water emulsion, water, an anhydrous carrier or an aqueous composition comprised of water and a carbopol type gel. Anhydrous vehicles are such as oils gelled with bentonite clays or oils gelled with silica. Water may be used alone or combined with a Carbopol TM type gel such as carbomer 910, carbomer 934P, carbomer 940, carbomer 941, which are either a polymer of acrylic acid crosslinked with an allyl ether of pentaerythritor or sucrose, magnesium aluminum silicate, PVP hydrogels. The former is the preferred vehicle.

The composition may additionally contain one or more of a solvent, solubilizer, protectant, pigment, metallic salt, humectant vitamin, conditioner emollients, humectants, thickeners, texturizers, solubilizing agents, preservatives, pigments, protectors, vitamins, conditioners, colorants, metallic salts, satabilizers or colorant.

The suitable solvents may be $C_{1-6}$ organic alcohols such as isopropanol, methanol, ethanol, isopropanol, N-methyl pyrrolidone, butyrolactone; or ethers, for example polyethylene glycol (PEG)-20 methyl glucose ether.

Solubilizers may be added to increase the solubility and consistency of the ingredients and may be selected from the glycols such as propylene glycol, butylene glycol, etc.

Various protectants may be added. The suitable protectants are well known to those skilled in the art. They may be such as polyvinyl pyrrolidone, allantoin, bisabolol, herbal and vegetal extracts, various humectants, including propylene glycol, hexylene glycol, glyceral, alkyl glucosides, alkoxylated alkyl glucosides, sorbitol, salts of hyaluronic acid, salts of pyrrolidone carboxylic acid, etc.

Various vitamins may be added for nutrient effects and include Calcium Pantothenate which is vitamin $B_6$ Salt.

The acceptable colorants are those generally known to be suitable in cosmetics such as the FD&C and D&C colors such as Blue #1, Yellow #5, Red #4 etc. Various preservatives may be added, including phenoxyethanol, alkyl esters of p-hydroxybenzoic acid, imidazolidinyl urea, quaternium-15, etc.

Conditioners may also be added to impart therapeutic properties. Alkoxylated lanolins, alkyl glucosides, cationic surfactants, amphoteric surfactants, solubilized vegetal extracts, proteins and derivatives thereof, etc.

The composition of the invention is best marketed in a kit or single container so that the consumer may purchase a specified amount to be used over a certain period of time.

A suitable nail stain removing kit is comprised of single units of porous material containing the dehydrated composition of the invention. The single unit is a small sponge preferably with abrasive properties. Abrasive polyester pads are excellent since they have a degree of abrasiveness to them. The pad is impregnated with the wet composition of the invention and then allowed to dry. A number of dehydrated pads maybe packed into a kit or suitable package form for sale to the consumer. The user merely moistens the pad with water and uses it to scrub the nails.

The composition may be also sold in a suitable container. For example, a small squeezable plastic tube is also an excellent vehicle. The tube may be filled with a small amount of the composition in a paste form. The tube is then purchased and used by the consumer.

Also, the composition may be sold in a container similar to a mascara tube which container contains a sponge or brush type applicator. The lid of the container, to which the applicator is attached is immersed into the composition when the cap is placed onto the tube. Upon removal of the cap from the tube, the attached applicator, containing the composition of the invention, may be applied directly to the nails and the applicator used as a scrubbing or cleansing vehicle.

The instant invention will be illustrated in accordance with the following examples which are set forth for the purposes of illustration only.

EXAMPLE 1

Nail Stain Remover #1

The following ingredients were combined in the following proportions to yield a slurry composition.

| Water Phase | W/W % | |
|---|---|---|
| | Pref'd. Amt. | Pref'd. Range |
| Water, deionized | 58.399 | 50–75 |
| Pumice, 2F Grade | 5.00 | 1–25 |
| Pumice, 4F Grade | 10.00 | 1–25 |
| Propylene Glycol | 10.00 | 1–15 |
| PEG-20 Methyl glucose ether | 10.00 | 1–15 |
| Titanium Dioxide | 5.00 | 1–15 |
| FD&C Blue #1 | 0.001 | 0.0001–0.005 |
| Triethanolamine | 0.50 | 0.10–2.50 |
| Phenoxy ethanol | 0.75 | 0.10–1.00 |
| Methyl paraben | 0.10 | 0.10–1.00 |
| Carbomer 940 | 0.25 | 0.10–1.00 |

EXAMPLE 2

Nail Stain Remover #2

The following ingredients were combined in the following proportions to yield a slurry composition

| Water Phase | W/W % | |
|---|---|---|
| | Pref'd. Amt. | Pref'd. Range |
| Water | 67.27 | 40–70 |
| Carbomer 940 | 0.75 | 0.1–1.5 |
| Propylene Glycol | 10.00 | 5–15 |
| PEG-20 Methyl Glucose Ether | 10.00 | 5–15 |
| Kaolin | 5.00 | 1–20 |
| Titanium Dioxide | 1.00 | 1–10 |
| Triethanolamine | 0.98 | 0.5–1.5 |
| Pumice 2F Grade | 5.00 | 1–10 |

EXAMPLE 3

Nail Stain Remover #3

The following ingredients were combined in the following proportions to yield a slurry

| Water Phase | W/W % | |
|---|---|---|
| | Pref'd. Amt. | Pref'd. Range |
| Water | 65.00 | 60–70 |
| Magnesium Aluminum Silicate | 2.00 | 1–10 |
| Trisodium EDTA | 5.00 | 1–10 |
| Talc | 2.00 | 1–3 |
| PVP | 0.50 | 0.5–2.00 |
| Zinc oxide | 4.00 | 1–10 |

We claim:

1. A composition useful for removing stains from human nails comprising
   (a) about 1–25 wt% of an abrasive agent
   (b) about 1–20 wt% of one or more white pigments in a cosmetically suitable vehicle selected from the group consisting of an aqueous solution of acrylic acid cross linked with the allyl ether of sucrose and an aqueous solution of acrylic acid cross linked with the allyl ether of pentaerythritol.

2. The composition of claim 1 wherein the cosmetically suitable vehicle is an aqueous solution, an oil in water emulsion, or an anhydrous carrier.

3. The composition of claim 2 additionally containing one or more emollients, humectants, thickeners, texturizers, solubilizing agents, preservatives, fragrances, pigments, protectors, vitamins, conditioners, colorants, metallic salts, or stabilizers.

4. The composition of claim 1 wherein the abrasive agent is pumice, polyethylene granules, aluminum oxide, silica, magnesium aluminum silicate, finely ground nutshells, diatomaceous earth, or kaolin.

5. The composition of claim 4 wherein the white pigments are zinc oxide, titanium dioxide, barium sulfate or zinc sulfide.

6. The composition of claim 5 wherein the abrasive agent is pumice or magnesium aluminum silicate.

7. A nail stain removing kit comprised of single units of porous material containing the dehydrated composition of claim 1 which unit is moistened with water immediately prior to use to yield a nail cleansing pad used to scrub the nails.

8. The kit of claim 7 wherein the unit of porous material comprises an abrasive polyester pad.

9. A nail stain removing kit comprised of a container filled with the composition of claim 1.

10. The kit of claim 9 wherein the composition is in a paster form.

11. The kit of claim 9 wherein the container is a squeezable plastic tube.

12. The kit of claim 9 wherein the container is a plastic screw cap tube containing an attached applicator.

13. A method for removing stains from human nails comprising cleansing nails with a nail stain removing composition comprising:
   (a) about 1–25 wt% of an abrasive agent
   (b) about 1–20 wt% of one or more white pigments in a cosmetically suitable vehicle selected from the group consisting of an aqueous solution of acrylic acid cross linked with the allyl ether of sucrose and an aqueous solution of acrylic acid cross linked with the allyl ether of pentaerythritol.

* * * * *